US012048782B2

(12) United States Patent
Sandford

(10) Patent No.: US 12,048,782 B2
(45) Date of Patent: Jul. 30, 2024

(54) FLUID CIRCUIT HAVING REDUCED PLASTICIZER MIGRATION

(71) Applicant: Fenwal, Inc., Lake Zurich, IL (US)

(72) Inventor: Craig Sandford, Buffalo Grove, IL (US)

(73) Assignee: Fenwal, Inc.

( * ) Notice: Subject to any disclaimer, the term of this patent is extended or adjusted under 35 U.S.C. 154(b) by 454 days.

(21) Appl. No.: 16/023,581

(22) Filed: Jun. 29, 2018

(65) Prior Publication Data

US 2019/0001026 A1    Jan. 3, 2019

Related U.S. Application Data

(60) Provisional application No. 62/527,709, filed on Jun. 30, 2017.

(51) Int. Cl.
*A61L 29/04* (2006.01)
*A61L 29/06* (2006.01)
(Continued)

(52) U.S. Cl.
CPC .............. *A61L 29/041* (2013.01); *A61L 29/06* (2013.01); *A61L 29/141* (2013.01); *A61M 1/0209* (2013.01); *A61M 1/0272* (2013.01); *A61M 1/3621* (2013.01); *A61M 1/3693* (2013.01); *A61M 39/08* (2013.01); *A61M 39/10* (2013.01); *B32B 27/22* (2013.01); *C08K 5/12* (2013.01); *F16L 11/12* (2013.01); *F16L 13/103* (2013.01); *A61M 1/362227* (2022.05); *A61M 1/36225* (2022.05); *A61M 1/362265* (2022.05); *A61M 2039/082* (2013.01); *C08K 5/0016* (2013.01)

(58) Field of Classification Search
CPC ......... F16L 11/12; F16L 13/103; B23B 27/22; A61L 29/141; A61L 29/041; A61L 29/06; A61M 1/0272

See application file for complete search history.

(56) References Cited

U.S. PATENT DOCUMENTS 4,120,449 A    10/1978  Brown et al.
4,216,856 A *   8/1980  Moring .................. B29D 29/06
                                                                    156/181

(Continued)

FOREIGN PATENT DOCUMENTS

EP              0686403 A1   12/1995
WO             8300699 A1    3/1983
WO          2014039086 A1    3/2014

OTHER PUBLICATIONS

Extended European Search Report dated Feb. 5, 2019 for European Application No. 18179990.9.

(Continued)

*Primary Examiner* — David Bochna
(74) *Attorney, Agent, or Firm* — Cook Alex Ltd.

(57) ABSTRACT

A fluid flow circuit assembly for a biological fluid processing device, comprising a PVC tubing comprising a polymeric plasticizer and/or a high molecular weight plasticizer having a molecular weight of 540 g/mol or more. The fluid flow circuit assembly also comprises a medical device component comprising a bond surface to which the PVC tubing is bonded by a solvent, wherein the bond surface comprises a polyester elastomer, plasticized PVC, and/or a polycarbonate.

10 Claims, 5 Drawing Sheets

(51) Int. Cl.
        *A61L 29/14*      (2006.01)
        *A61M 1/02*       (2006.01)
        *A61M 1/36*       (2006.01)
        *A61M 39/08*      (2006.01)
        *A61M 39/10*      (2006.01)
        *B32B 27/22*      (2006.01)
        *C08K 5/12*       (2006.01)
        *F16L 11/12*      (2006.01)
        *F16L 13/10*      (2006.01)
        *C08K 5/00*       (2006.01)

(56)    References Cited

U.S. PATENT DOCUMENTS 4,948,643    A  *   8/1990   Mueller ................ A61L 29/085
                                                                    428/36.6
    5,702,383    A  *   12/1997  Giesler ............... A61M 1/0236
                                                                    128/898
    5,996,634    A      12/1999  Dennehey et al.
    9,062,803    B2 *   6/2015   Bourgeois ........... B29C 66/1224
    2005/0148993 A1 *   7/2005   Mathias ........... A61B 5/150503
                                                                    600/573
    2013/0190714 A1 *   7/2013   Bourgeois ................ B32B 1/08
                                                                    604/500
    2014/0212666 A1 *   7/2014   Dakka ...................... C07C 2/76
                                                                    560/76
    2017/0261132 A1 *   9/2017   Garver ..................... B32B 7/12

OTHER PUBLICATIONS

Welle et al., "Migration of plasticizers from PVC tubes into enteral feeding solutions", Pharma Int., (2016), p. 17-21, Mar. 2005.

* cited by examiner ly rigid or brittle, a plasticizer may be incorporated into the PVC. Examples of plasticizers for medical grade PVC include DEHP and TEHTM.

FLUID CIRCUIT HAVING REDUCED PLASTICIZER MIGRATION

CROSS-REFERENCE TO RELATED APPLICATIONS

This application claims the benefit of U.S. Provisional Patent App. No. 62/527,709 filed Jun. 30, 2017, which is expressly incorporated herein by reference in its entirety.

FIELD OF THE DISCLOSURE

The present disclosure relates generally to systems and methods of processing biological fluid components and, in particular to systems and methods for biological fluid disposable sets having reduced plasticizer migration.

BACKGROUND

Whole blood may be separated into various components, such as red blood cells, white blood cells, platelets, plasma, etc. In blood processing systems, whole blood may be drawn from a donor/patient, the particular blood component or constituent removed and collected, and the remaining blood constituents returned to the donor. By removing only particular constituents, less time may be needed for the donor's body to return to normal, and donations may be made at more frequent intervals than when whole blood is collected. The overall supply of blood constituents, such as plasma and platelets, may thereby be increased and be made available for health care.

Blood may be separated into its constituents through centrifugation. Whole blood may be passed through a centrifuge after it is withdrawn from, and before it is returned to, the donor. To avoid contamination, the blood may be contained within a sealed, sterile fluid flow system during the entire centrifugation process. Blood processing systems may thus include a permanent, reusable centrifuge assembly or "hardware" that spins and pumps the blood, and a disposable, sealed and sterile fluid processing or fluid circuit assembly that actually makes contact with the blood. The centrifuge assembly may engage and spin a portion of the fluid processing assembly (often called the centrifuge/separation chamber) during a collection procedure. The blood, however, may make actual contact only with the disposable fluid processing assembly, which may be used only once and then discarded.

The disposable fluid processing assembly may comprise sealed containers/bags and processing components connected together by flexible tubing. The containers and flexible tubing are usually made of a plastic material. Containers and tubing approved for the collection of blood and the storage of blood components may often be made of a polyvinyl chloride (PVC). Due to the fact that PVC can be somewhat rigid or brittle, a plasticizer may be incorporated into the PVC. Examples of plasticizers for medical grade PVC include DEHP and TEHTM.

SUMMARY

According to an exemplary embodiment, the present disclosure is directed to a fluid flow circuit assembly for a biological fluid processing device, comprising a PVC tubing comprising a polymeric plasticizer and/or a high molecular weight plasticizer having a molecular weight of 540 g/mol or more. The fluid flow circuit assembly also comprises a medical device component comprising a bond surface to which the PVC tubing is bonded by a solvent, wherein the bond surface comprises a polyester elastomer, plasticized PVC, and/or a polycarbonate.

According to an exemplary embodiment, the present disclosure is directed to an umbilicus for conveying fluid between components of a biological fluid flow circuit assembly. The umbilicus comprises an elongated body having a first end and a second end and a fluid-transmitting lumen comprising a first surface extending between the first and second ends. The umbilicus also comprises a PVC tubing segment comprising a polymeric plasticizer and/or a high molecular weight plasticizer having a molecular weight of 540 g/mol or more. The tubing segment comprises a second surface adhered by way of a bond to the first surface of the lumen at the first end.

According to an exemplary embodiment, the present disclosure is directed to a fluid flow circuit assembly for a centrifugal blood separator, comprising a PVC tubing comprising an acrylate copolymer and/or a TEHTM plasticizer and a medical device component comprising a bond surface to which the PVC tubing is bonded by a solvent. The bond surface comprises a thermoplastic block polyester copolymer, plasticized PVC, and/or a polycarbonate.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

Figure 1:
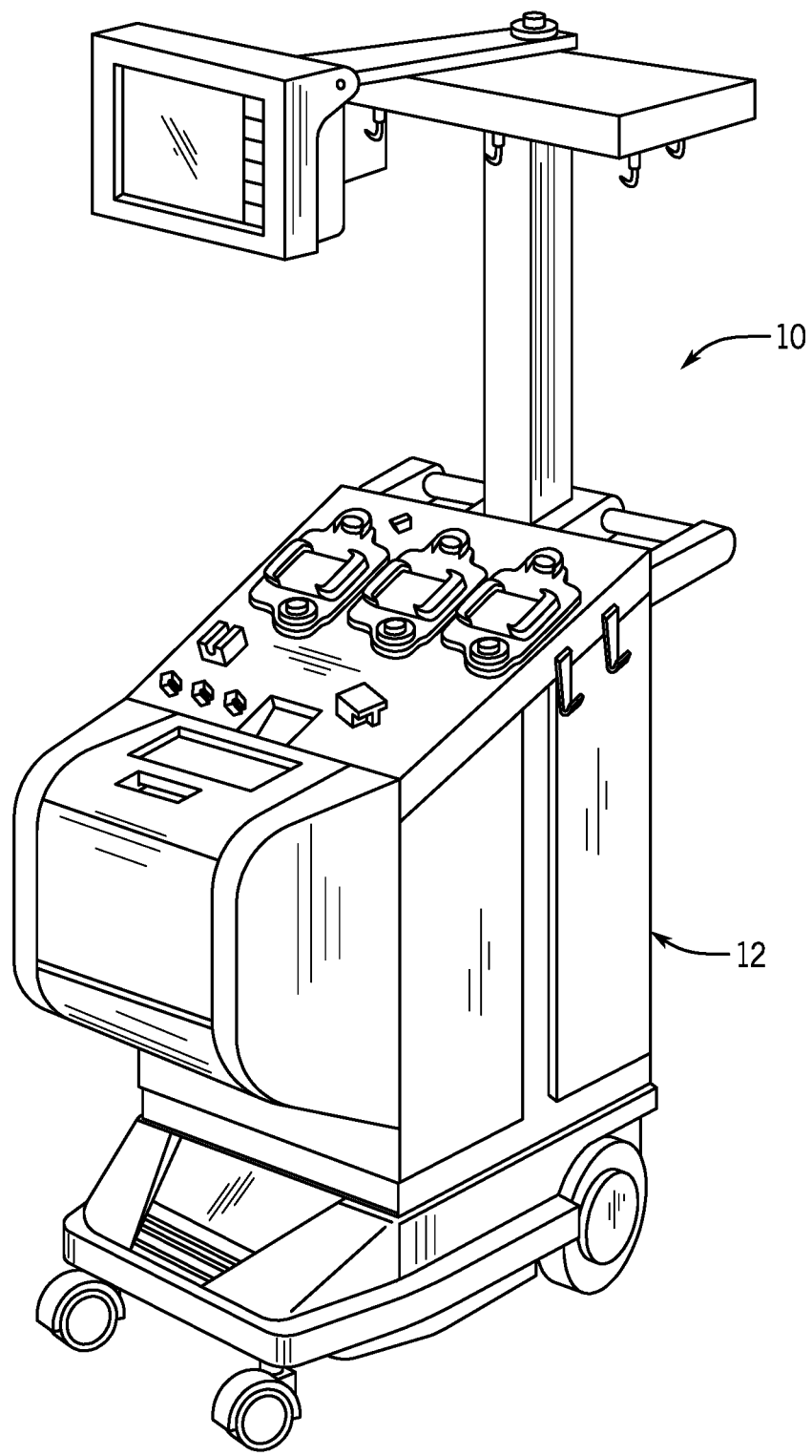
FIG. 1 is a perspective view of a durable fluid processing system that may be used in combination with an umbilicus, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may minimize leaks associated with PVC medical tubing bonds.

Some embodiments may decrease migration of plasticizer from PVC medical tubing onto the medical device surface onto which the tubing is bonded.

Some embodiments may strengthen longevity of bonds between PVC medical tubing and medical device bonding surfaces.

Blood processing systems may utilize centrifugal or membrane separation systems to separate blood components. An example of a membrane separator is disclosed in PCT Patent Application Publication No. WO 2014/039086 A1, which is incorporated by reference in its entirety. In one embodiment of a centrifugal separation system, a centrifuge may operate on a "one-omega, two-omega" operating principle. This principle is disclosed in detail in U.S. Pat. No. 4,120,449 to Brown et al. and U.S. Pat. No. 5,996,634 to Dennehey et al., which are hereby incorporated by reference in their entireties. A system such as the ones described in Brown and Dennehey may enable a centrifuge to spin a sealed, closed system without a need for rotating seals and allow preservation of sterility and sealed integrity of the fluid processing assembly. Centrifugal blood processing systems may include a fluid processing assembly that includes a plastic bag or molded chamber that is spun in the centrifuge and that is connected to a blood source or blood donor and to a stationary portion of the centrifuge assembly through an elongated member that may be made up of one or more plastic tubes. The elongated member is commonly referred to as an "umbilicus" and may be arranged with both of its end portions coaxially aligned with the axis of rotation of the centrifuge. The centrifuge chamber may be rotated at "two-omega" RPM and the umbilicus may be orbited around the centrifuge chamber at "one-omega" RPM. One end of the umbilicus may therefore be stationary, the other end may rotate at a two-omega speed with the centrifuge chamber to which it is attached, and the intermediate portion or midsection of the umbilicus may orbit about the chamber at a one-omega speed. The sealed, sterile integrity of the fluid processing assembly may thus be maintained without the need for rotating seals while preventing the end of the umbilicus connected to the blood source or donor from twisting up as the separation chamber is spun.

An umbilicus may comprise a unitarily formed (generally by an extrusion process) main body defining one or more fluid-transmitting lumen. The body may be formed of a material specially selected to perform the several required functions of the umbilicus, including being flexible enough to assume the proper orientation with regard to the centrifuge assembly, rigid enough to serve as a drive mechanism for rotating the processing chamber, and having a torsional stiffness leading to the aforementioned "untwisting" at the proper two-omega speed during fluid processing. One material that may be used in forming the umbilicus is a thermoplastic polyester elastomeric material, such as Hytrel, available from E.I. DuPont de Nemours & Company. Plasticized polyvinyl chloride ("PVC") tubing connecting the umbilicus to the remainder of the fluid circuit assembly may be bonded to the end blocks by various bonding mechanisms.

FIG. 1 shows a centrifugal fluid processing device or system 10 that may be used in combination with a fluid processing circuit having an umbilicus according to the present disclosure, although it should be understood that other fluid processing systems may be employed without departing from the scope of the present disclosure. The system 10 may be used for processing various biological fluids, such as whole blood, blood components, and/or other suspensions of biological cellular materials. The system 10 may include a centrifuge assembly 12 for separating a fluid into its constituent parts.

Figure 2:
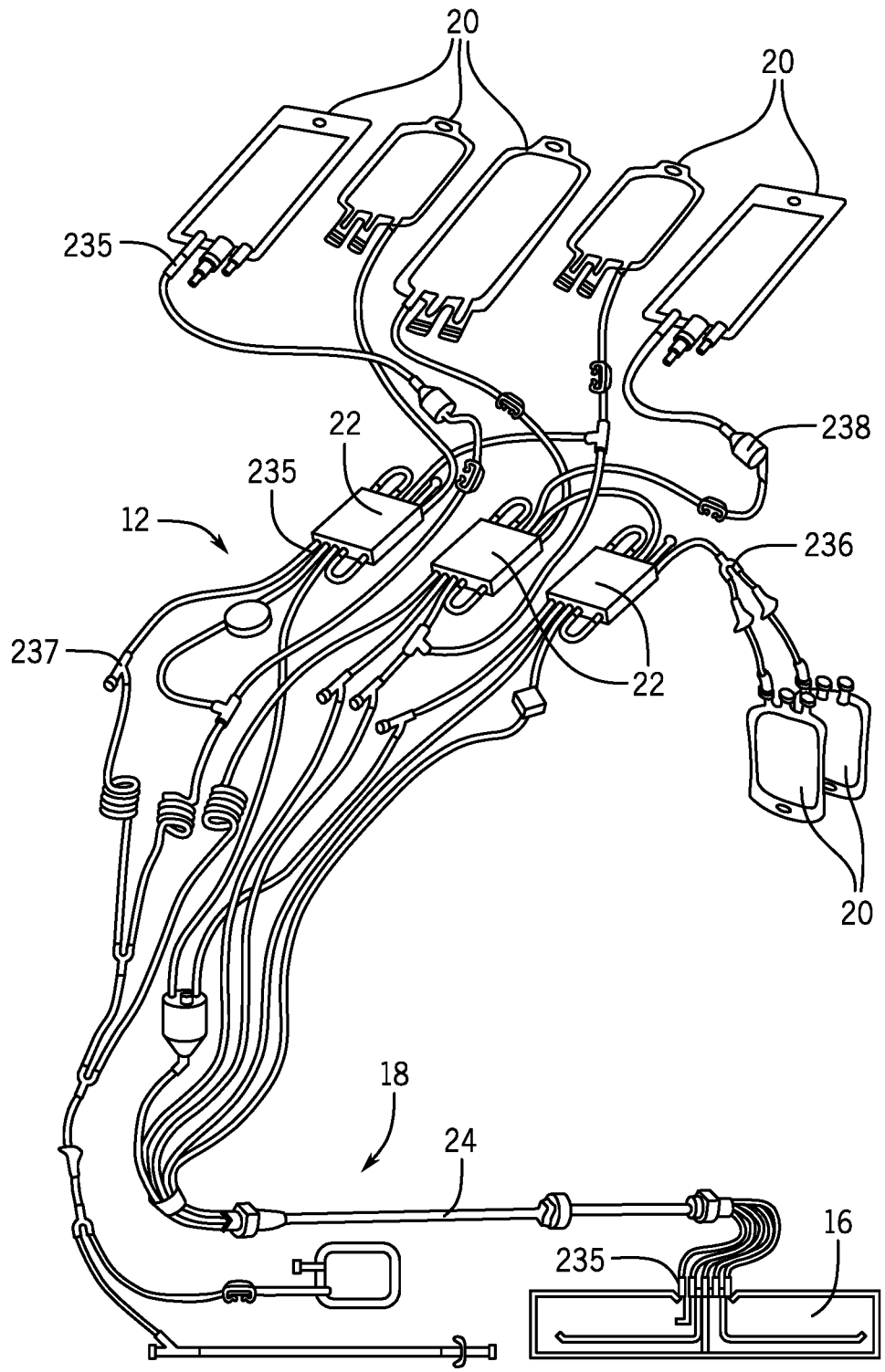
FIG. 2 is a perspective view of a disposable fluid processing assembly usable in association with the durable fluid processing system of FIG. 1, according to an exemplary embodiment.
Figure 3:
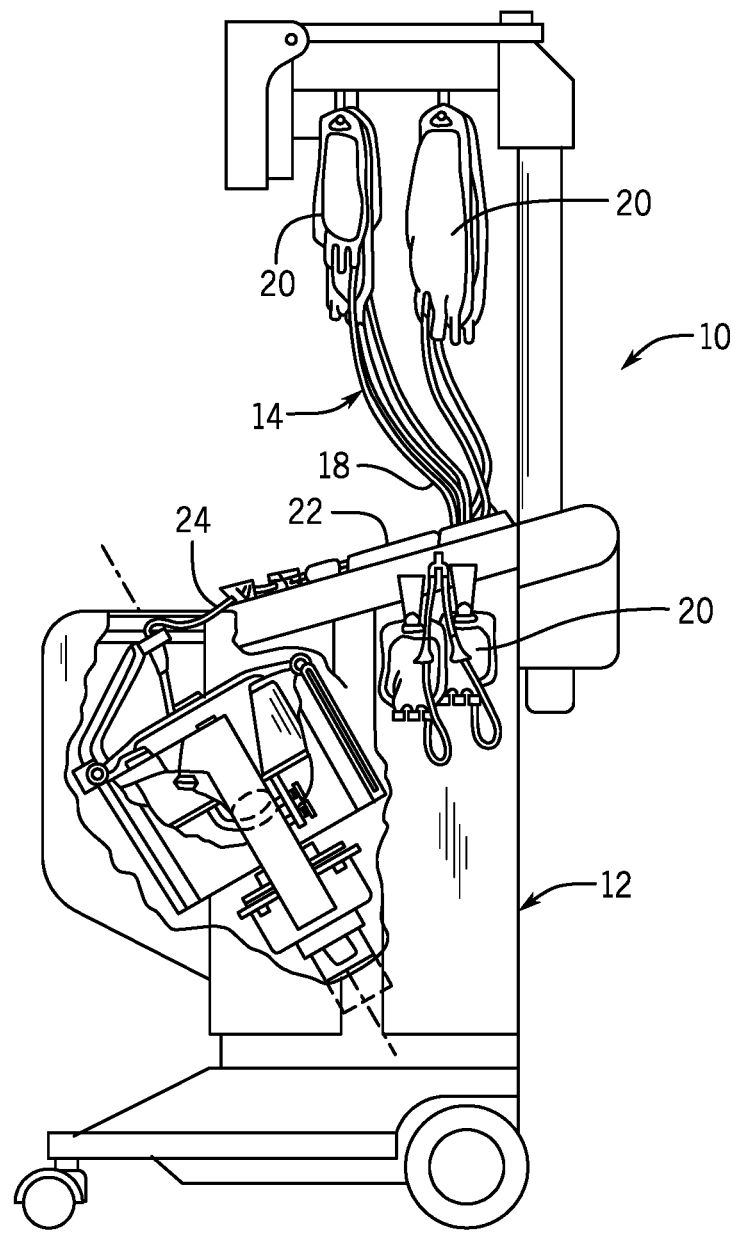
FIG. 3 is a side elevational view of the disposable fluid processing assembly of FIG. 2 mounted on the durable fluid processing system of FIG. 1, which is partially broken away, according to an exemplary embodiment.

The durable fluid processing system 10 may be used in combination with a disposable processing set or fluid circuit 14, an example of which is shown in FIG. 2. FIG. 3 shows the disposable set 14 mounted on the durable system 10. The disposable set 14 may be a single use, disposable item loaded on the system 10 at the time of use. After a fluid processing procedure has been completed, the operator may remove the disposable set 14 from the system 10 and discard components that are no longer needed.

The disposable set 14 may include a processing chamber 16 (FIG. 2) and associated fluid flow tubing, containers, and other components. In use, the centrifuge assembly 12 may rotate the processing chamber 16 to centrifugally separate blood components. Whole blood may be conveyed to the processing chamber 16 from a donor or from another source of blood (such as a bag of collected blood), and separated blood components may be conveyed from the processing chamber 16, through a plurality of flexible tubes that form part of a fluid circuit 18. The fluid circuit 18 may further include a plurality of containers 20 that may be supported by elevated hangers located over the centrifuge assembly 12 (see FIG. 3) and dispense and receive liquids during processing. Fluid flow through the fluid circuit 14 may be controlled in a variety of ways. For example, fluid flow may be controlled via cassettes 22 with pre-formed fluid passageways, which may be selectively opened and closed pneumatically, hydraulically, and/or by movable actuators. Cassettes 22 may operate in association with valve and pump stations on the centrifuge assembly 12 to direct liquid flow among multiple liquid sources and destinations during a blood processing procedure. Tubes connected to the processing chamber 16 may lead to a flexible umbilicus 24, with additional tubes at the other end of the umbilicus 24 fluidly connecting the processing chamber 16 (via the umbilicus 24) to the remainder of the disposable set 14, including the containers 20 and the cassettes 22. The umbilicus 24 is shown separately from the disposable set in FIG. 4.

Figure 4:
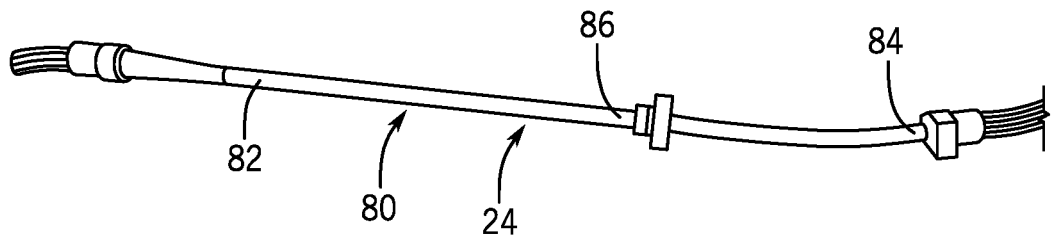
FIG. 4 is a side view of an umbilicus, according to an exemplary embodiment.

FIG. 4 shows the umbilicus 24 isolated from the remainder of the disposable set 14. The umbilicus 24 may comprise and consolidate the multiple fluid paths leading to and from the processing chamber 16, although it may also have a single flow path. The umbilicus 24 may provide a continuous, sterile environment for fluids (such as blood and blood components) to pass. In construction, the umbilicus 24 may preferably be flexible enough to function in the relatively small, compact operating space that the centrifuge assembly 12 provides. The umbilicus 24 may preferably be durable enough to withstand significant flexing and torsional stresses imposed by the small, compact spinning environment, where continuous rotation rates of several thousand revolutions per minute may typically be encountered for long periods of time.

Figure 5:
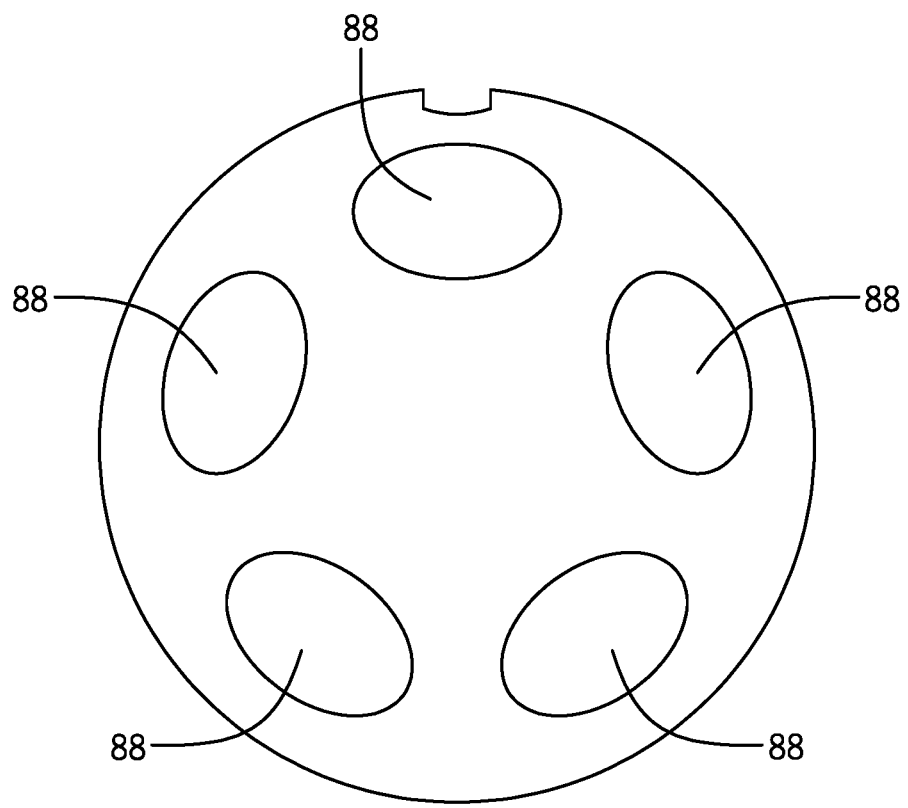
FIG. 5 is a cross-sectional view of an end of the umbilicus of FIG. 4, according to an exemplary embodiment.

Referring to FIGS. 4 and 5, the umbilicus body 80 may define one or more fluid-transmitting lumen 88 extending between the ends 82 and 84, as can be seen in FIG. 5, which shows five fluid-transmitting lumen 88 extending through the midsection 86, which may be equal to the number of flow paths (which may be separate tubes or a single tube with multiple lumen or a combination of tubes with single and/or multiple lumen) connecting each end 82, 84 of the umbilicus 24 to the remainder of the disposable set 14 (as best illustrated in FIG. 2). Each lumen 88 may be associated (in fluid flow communication) with one of the tubes or lumen leading into the processing chamber 16 at the second end 84 of the umbilicus body 80, and may also be associated with one of the tubes or lumen leading to the remainder of the disposable set 14 at the first end 82 of the umbilicus body 80. Accordingly, the number of lumen 88 defined in the umbilicus body 80 may vary according to the number of tubes or lumen leading from the umbilicus 24 to the processing chamber 16 and the remainder of the disposable set 14.

Figure 6:
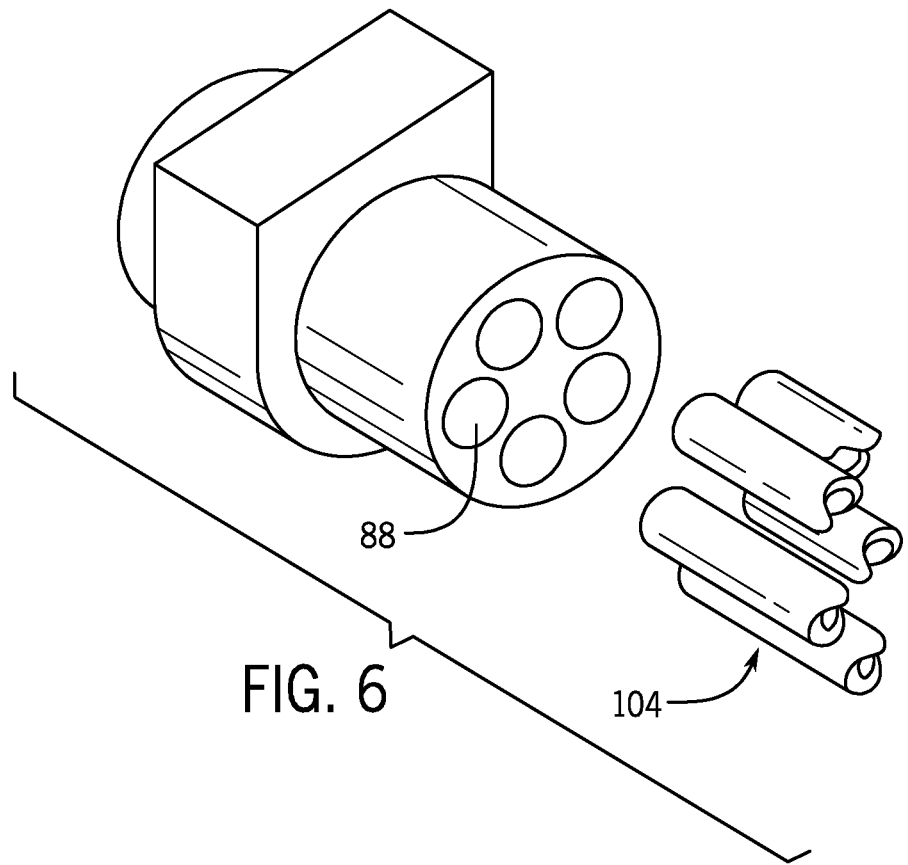
FIG. 6 is a perspective view of an end of the umbilicus of FIG. 4, having a plurality of tubing segments associated therewith, according to an exemplary embodiment.
Figure 7:
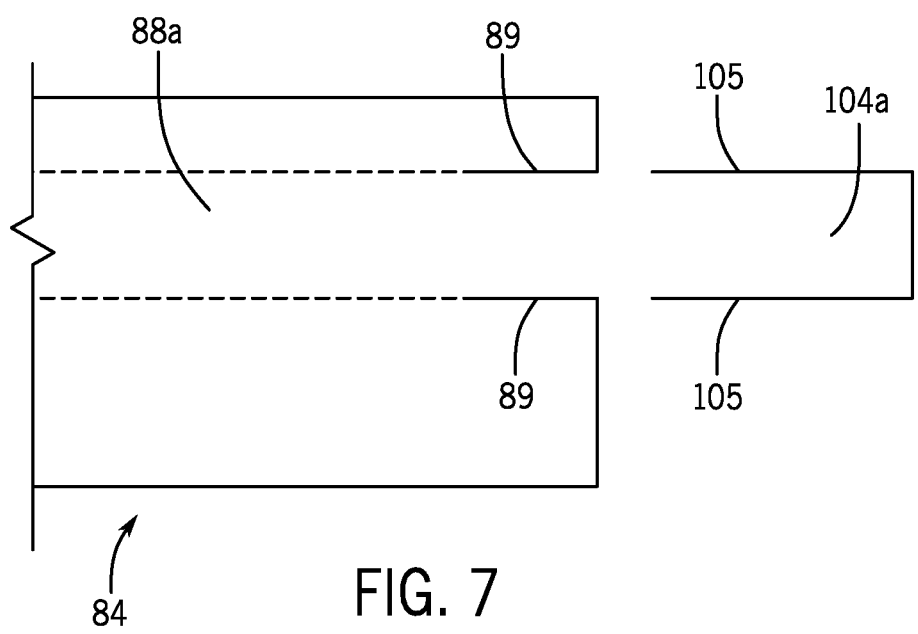
FIG. 7 is an enlarged broken away view of a lumen of an umbilicus and its associated tubing segment, according to an exemplary embodiment.

FIG. 6 shows tubing segments 104 received within the lumen 88 at the second end 84 of the umbilicus body 80. In one embodiment, a solvent (e.g., cyclohexanone, methylethylketone) or other suitable bond-forming compound may be applied to the ends of the lumen 88 and a portion of a tubing segment 104 may be inserted into each lumen end. FIG. 7 is an enlarged view of a single tubing segment 104a and its associated lumen 88a prior to bonding. In one embodiment, the bond used may be a solvent bond, and the outer surface 105 of tubing segment 104a and the inner surface 89 of lumen 88a may be sealed together utilizing a strong solvent, such as cyclohexanone and/or methylethylketone, which temporarily softens and/or dissolves the material of the outer surface 105 and the inner surface 89 during which surfaces 105 and 89 may bond together before hardening.

Subsequent plasticizer migration during the shelf life and/or use of the medical fluid circuit may be mitigated by utilizing PVC tubing comprising a high molecular weight plasticizer and/or a polymeric plasticizer. Plasticizer migration may compromise a solvent bond and lead to leakage as molecules or polymer chains forming part of the bond migrate, e.g., to the medical device bond surface to which the tubing is bonded, leaving holes where they originated. Incorporation of polymeric plasticizers and/or high molecular weight plasticizers may lead to decreased migration. For purposes of this description, a high molecular weight plasticizer is a plasticizer having a molecular weight of at least 540 g/mol. It may also be advantageous for the plasticizer to have an overall three dimensional structure resistant to migration while maintaining compatibility with PVC. Resistance to migration may be enhanced by incorporating a plasticizer comprising more than two aliphatic chains, where each chain comprises at least six carbons. One example of a high molecular weight plasticizer having a suitable overall three dimensional structure exhibiting lower migration properties is Tri-(2-ethylhexyl) trimellitate (TEHTM), which has a molecular weight of 546 g/mol. One example of a polymeric plasticizer having a suitable overall three dimensional structure exhibiting lower migration properties is an acrylate copolymer, such as Elvaloy, available from E.I. DuPont de Nemours & Company, although any suitable polymer for plasticizing PVC may be used. PVC tubing incorporating a high molecular weight plasticizer and/or polymeric plasticizer may be manufactured by any suitable known extrusion processes.

Referring to FIG. 7, tubing segment 104a that is to be bonded with the inner surface 89 of lumen 88a may comprise a high molecular weight plasticizer and/or a polymeric plasticizer, e.g., TEHTM, Elvaloy. In one embodiment, the inner surface 89 may comprise a copolyester elastomer, such as a thermoplastic polyester elastomer. In one embodiment, the thermoplastic polyester elastomer may be a block copolymer, such as Hytrel. A solvent may be applied to the outer surface 105 of tubing segment 104a. The solvent may be any suitable compound capable of at least partially solvent bonding the surfaces 89 and 105. In an embodiment in which surfaces 89 and 105 respectively comprise Hytrel and TEHTM, cyclohexanone and/or methylethylketone may be used. The tubing segment 104a may be inserted into the lumen 88a and contact the surface 89 to bond with the outer surface 105.

Although the medical device bond surface to which PVC tubing is bonded has been described in the context of an inner surface of a lumen of an umbilicus, it should be understood that the aforementioned system and method may be applied in the context of any medical device component to which PVC tubing may be connected. For example, referring to FIG. 2, PVC tubing comprising polymeric plasticizers and/or high molecular weight plasticizers may be bonded to an inner or outer surface of a port 235, a y-connector 236, and/or adapters 237, 238. In an embodiment in which cyclohexanone or methylethylketone is used as the tubing solvent, the inner or outer surface of e.g., the port 235, a y-connector 236, and/or adapters 237, 238 to which the PVC tubing may be bonded may also comprise polycarbonate and/or plasticized PVC.

Without limiting the foregoing description, in accordance with a first aspect of the subject matter herein, there is provided a fluid flow circuit assembly for a biological fluid processing device, comprising a PVC tubing comprising a polymeric plasticizer and/or a high molecular weight plasticizer having a molecular weight of 540 g/mol or more. The fluid flow circuit assembly also comprises a medical device component comprising a bond surface to which the PVC tubing is bonded by a solvent. The bond surface comprises a polyester elastomer, plasticized PVC, and/or a polycarbonate.

In accordance with a second aspect which may be used or combined with the immediately preceding aspect, the biological fluid processing device comprises a centrifugal blood separator, and the medical device component comprises an umbilicus comprising a thermoplastic polyester elastomeric material.

In accordance with a third aspect which may be used or combined with any of the preceding aspects, the solvent comprises cyclohexanone and/or methylethylketone.

In accordance with a fourth aspect which may be used or combined with the immediately preceding aspect, the bond surface comprises at least one of a thermoplastic polyester elastomer, a polycarbonate, and/or plasticized PVC.

In accordance with a fifth aspect which may be used or combined with any of the preceding aspects, the polymeric plasticizer comprises an acrylate copolymer.

In accordance with a sixth aspect which may be used or combined with any of the preceding aspects, the medical device component comprises a port, y-connector, or adapter.

In accordance with a seventh aspect which may be used or combined with any of the preceding aspects, the medical device component comprises an umbilicus having a plural number of lumen at one end of the umbilicus that is equal to a number of the PVC tubing in communication between the one end to a remainder of the fluid flow circuit assembly.

In accordance with an eighth aspect which may be used or combined with any of the preceding aspects, the plasticizer comprises more than two aliphatic chains, wherein each of the more than two aliphatic chains comprises at least six carbons.

In accordance with a ninth aspect, there is provided an umbilicus for conveying fluid between components of a biological fluid flow circuit assembly. The umbilicus comprises an elongated body having a first end and a second end and a fluid-transmitting lumen comprising a first surface extending between the first and second ends. The umbilicus also comprises a PVC tubing segment comprising a polymeric plasticizer and/or a high molecular weight plasticizer having a molecular weight of 540 g/mol or more. The tubing segment comprises a second surface adhered by way of a bond to the first surface of the lumen at the first end.

In accordance with a tenth aspect which may be used or combined with the immediately preceding aspect, the first surface comprises an annular inner surface of the fluid-transmitting lumen, and the second surface comprises an outer surface of the tubing segment.

In accordance with an eleventh aspect which may be used or combined with the ninth or tenth aspect, the tubing segment comprises at least one of a polyester elastomer, plasticized PVC, and a polycarbonate.

In accordance with a twelfth aspect which may be used or combined with any of the ninth through eleventh aspects, the tubing segment comprises at least one of an acrylate copolymer and a TEHTM plasticizer.

In accordance with a thirteenth aspect which may be used or combined with any of the ninth through twelfth aspects, the bond between the first and second surfaces comprises a solvent bond comprising a solvent and softened and subsequently hardened PVC.

In accordance with a fourteenth aspect which may be used or combined with the immediately preceding aspect, the solvent comprises cyclohexanone and/or methylethylketone.

In accordance with a fifteenth aspect which may be used or combined with any of the ninth through fourteenth aspects, the polymeric plasticizer comprises an acrylate copolymer.

In accordance with a sixteenth aspect which may be used or combined with any of the ninth through fifteenth aspects, a plural number of lumen at the first end of the umbilicus is equal to a number of the PVC tubing segments in communication between the plural number of lumen and a remainder of the biological fluid flow circuit assembly.

In accordance with a seventeenth aspect, there is provided a fluid flow circuit assembly for a centrifugal blood separator, comprising a PVC tubing comprising an acrylate copolymer and/or a TEHTM plasticizer. The PVC tubing is bonded by a solvent to a bond surface of a medical device component. The bond surface comprises a thermoplastic block polyester copolymer, plasticized PVC, and/or a polycarbonate.

In accordance with an eighteenth aspect which may be used or combined with the immediately preceding aspect, the medical device component comprises an umbilicus for conveying fluid between components of the fluid flow circuit In accordance with a nineteenth aspect which may be used or combined with the immediately preceding aspect, the umbilicus comprises a plural number of lumen at one end of the umbilicus that is equal to a number of tubing in communication between the one end to a remainder of the fluid flow circuit assembly.

In accordance with a twentieth aspect which may be used or combined with any of the seventeenth through nineteenth aspects, the bond surface comprises an annular inner surface of the medical device component and an outer surface of the PVC tubing.

In accordance with a twenty-first aspect which may be used or combined with any of the seventeenth through twentieth aspects, the bond surface comprises a solvent bond comprising cyclohexanone and/or methylethylketone.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A fluid flow circuit assembly for a centrifugal blood separator, comprising:
   a PVC tubing comprising a plasticizer incorporated into said PVC tubing, wherein said plasticizer is an acrylate copolymer;
   a medical device component comprising a bond surface to which the PVC tubing is bonded by a solvent;
   wherein the bond surface comprises a thermoplastic block polyester copolymer, plasticized PVC, and/or a polycarbonate;
   wherein the plasticizer is resistant to plasticizer migration between the bond surface of the medical device and an outer surface of the plasticized PVC tubing; and
   wherein the plasticizer comprises more than two aliphatic chains, wherein each of the more than two aliphatic chains comprises at least six carbons.

2. The fluid flow circuit assembly of claim 1, wherein the medical device component comprises an umbilicus comprising a thermoplastic polyester elastomeric material for conveying fluid between components of the fluid flow circuit.

3. The fluid flow circuit assembly of claim 2, wherein the umbilicus comprises a plural number of lumen at one end of the umbilicus that is equal to a number of tubing in communication between the one end to a remainder of the fluid flow circuit assembly.

4. The fluid flow circuit assembly of claim 1, wherein the bond surface comprises an annular inner surface of the medical device component and an outer surface of the PVC tubing.

5. The fluid flow circuit assembly of claim 1, wherein the solvent comprises cyclohexanone and/or methylethylketone.

6. A fluid flow circuit assembly for a centrifugal blood separator, comprising:
   A PVC tubing comprising a single plasticizer incorporated into said PVC tubing, wherein said single plasticizer is a TEHTM plasticizer;
   a medical device component comprising a bond surface to which the PVC tubing is bonded by a solvent, wherein the bond surface comprises a thermoplastic block polyester copolymer, plasticized PVC, and/or a polycarbonate; and
   wherein the plasticizer is resistant to plasticizer migration between the bond surface of the medical device and an outer surface of the plasticized PVC tubing; and
   wherein the single plasticizer comprises more than two aliphatic chains, wherein each of the more than two aliphatic chains comprises at least six carbons.

7. The fluid flow circuit assembly of claim 6, wherein the medical device component comprises an umbilicus comprising a thermoplastic polyester elastomeric material for conveying fluid between components of the fluid flow circuit.

8. The fluid flow circuit assembly of claim 7, wherein the umbilicus comprises a plural number of lumen at one end of the umbilicus that is equal to a number of tubing in communication between the one end to a remainder of the fluid flow circuit assembly.

9. The fluid flow circuit assembly of claim 6, wherein the bond surface comprises an annular inner surface of the medical device component and an outer surface of the PVC tubing.

10. The fluid flow circuit assembly of claim 6, wherein the solvent comprises cyclohexanone and/or methylethylketone.

* * * * *